US006673349B2

(12) United States Patent
Barteling

(10) Patent No.: US 6,673,349 B2
(45) Date of Patent: Jan. 6, 2004

(54) METHOD OF INACTIVATING MICROORGANISMS

(76) Inventor: Simon Johannes Barteling, Nieuwe Keizersgracht 438, Amsterdam (NL), NL-1018 VG ( * ) Notice: Subject to any disclaimer, the term of this patent is extended or adjusted under 35 U.S.C. 154(b) by 0 days.

(21) Appl. No.: 10/168,468

(22) PCT Filed: Dec. 18, 2000

(86) PCT No.: PCT/ZA00/00254

§ 371 (c)(1),
(2), (4) Date: Sep. 19, 2002

(87) PCT Pub. No.: WO01/46390

PCT Pub. Date: Jun. 28, 2001

(65) Prior Publication Data

US 2003/0035811 A1 Feb. 20, 2003

(30) Foreign Application Priority Data

Dec. 20, 1999 (ZA) .............................. 99/7757

(51) Int. Cl.[7] ...................... A61K 39/00; A61K 39/12; A61K 39/125; C12N 7/06; C12N 1/06; A61L 2/00

(52) U.S. Cl. ................................ 424/184.1; 424/204.1; 424/216.1; 435/239; 435/259; 422/28; 422/36

(58) Field of Search ................. 435/239, 259, 435/4, 5, 40.5; 424/184.1, 204.1, 234.1, 216.1; 422/36, 28

(56) References Cited

U.S. PATENT DOCUMENTS

| 3,636,196 A | | 1/1972 | Bauer et al. | |
|---|---|---|---|---|
| 5,069,901 A | * | 12/1991 | Jones et al. | ..................... 435/5 |
| 5,242,686 A | | 9/1993 | Chu et al. | |
| 5,698,432 A | * | 12/1997 | Oxford | ........................ 435/236 |

FOREIGN PATENT DOCUMENTS

| GB | 1256456 | | 5/1969 | | |
|---|---|---|---|---|---|
| WO | 97/31093 | * | 8/1997 | ............ | C11D/3/48 |

OTHER PUBLICATIONS

Bahnemann (Vaccine 8: 299–303, 1990).*
Brown (Develop. Biol. Standard. 75:37–41, 1990).*
Race et al (Vaccine 13: 54–60, 1995).*
Rolands et al (Archiv. fur die gesamte virusforshung 39:274–283, 1972).*
Mowat, G.N. et al, "Enhancement of Immunizing Potency of a Foot–and–Mount Disease Vaccine for Cattle by Treatment of the Antigen with Formaldehyde" Archiv Fur die gesamte Virusforschung, 41, 365–370 (1973).
Shvartsman, P., et al; "Study of mechanisms of inactivation and mutagenesis induced by ethylenimine on sex cells of Drosophila"; Genetika (1982), 18(6), 967–76 (Abstract).
Fontaine, J.; "Inactivation of Aphteux virus. Effects of inactivating agent on virion preservation"; Proc. World Vet. Congr. 20th (1975) Vol. 2, 1435–54 (Abstract).

* cited by examiner

*Primary Examiner*—Mary E. Mosher
(74) *Attorney, Agent, or Firm*—McDonnell Boehnen Hulbert & Berghoff

(57) ABSTRACT

This invention provides methods of inactivating a microorganism and preparing a vaccine including the step of applying to said microorganism a cross-linking agent simultaneously with a separate inactivant. This invention further relates to vaccines prepared by such methods and a kit including such inactivated microorganism. The cross-linking agent is typically formaldehyde (FA) and the inactivant typically binary ethyleneimine (BEI).

28 Claims, 1 Drawing Sheet

Figure 1: Inactivation plots obtained with BEI alone (a) for one of the SAT vaccine strains and with BEI-FA (b – f) for 5 vaccine strains.

METHOD OF INACTIVATING MICROORGANISMS

INTRODUCTION AND BACKGROUND TO THE INVENTION

This invention relates to methods of inactivating microorganisms and manufacturing vaccines, to vaccines manufactured by such methods, and to kits incorporating such inactivated microorganisms. More particularly but not exclusively, this invention relates to methods of inactivating viruses and manufacturing virus vaccines and to vaccines manufactured from such methods.

Virus inactivation and safety tests are the most critical steps in the production of inactivated vaccines, in the case of foot-and-mouth disease (FMD) vaccines in particular, guaranteed safety is essential because any occurrence of the disease will cause a blockade of all export trade of animals and animal products.

A classical method of inactivating FMD virus and preparing FMD vaccine is with formaldehyde as described by Waldmann et al.: Waldmann O, Pyl G, Hobohm K O, Mohlmann H: "Die Entwicklung des Riemser Adsorbatimpfstoffes gegen Maul—und Klauenseuche und seine Herstellung". Zbl Bakt I Orig 148: 1, 1941.

In the past this method was used in the preparation of FMD vaccines and e.g. applied in the preparation of vaccine based on Frenkel cultures; Frenkel S: "Modifications de la méthode de culture du virus aphteuse selon Frenkel. Valeur des vaccins selon les données du laboratoire". Bull OIE 1: 985, 1964.

Formaldehyde is known for its cross-linking action (fixation) of proteins, which probably caused the high stability and long shelf lives—of up to 5 years or longer—of FA-inactivated (Frenkel) vaccines.

Several studies showed that at the FA concentration prescribed by Waldmann, inactivation plots were not linear and often showed "tailing off", which may cause incomplete inactivation. This was demonstrated in the following publications:

Graves J H: "Formaldehyde inactivation of foot-and-mouth disease virus as applied to vaccine preparation", Am J Vet Res 24, 1131;

Weslen, T. and Dinter, Z.: "The inactivation of foot-and-mouth disease virus by formalin". Arch. Ges. Virusforsch. 1957, 7, 394;

Barteling S J, Woortmeijer R, Visser N: "Innocuity testing of foot-and-mouth disease vaccines. I. Formaldehyde-inactivated alhydrogel vaccines", J Biol. Stand. 1983, 11, 297.

Formaldehyde-inactivated vaccines induced good immunity and it was shown that under well-defined conditions linear inactivation plots can be obtained with FA (Barteling S J, Woortmeijer R: "Formaldehyde inactivation of foot-and-mouth disease virus. Conditions for the preparation of safe vaccine", Arch Virol. 19B4, 80, 103). However, inactivation with FA remained suspicious and inactivation by aziridins (e.g. acetyl-ethylenimine, AEI) which more rapidly inactivates, with linear inactivation plots, became the method of choice.

Inactivation with AEI is described in the following publication:

Brown F, Hyslop NSG, Crick J, Morrow A W: "The use of acetyl-ethyleneimine in the production of inactivated foot-and-mouth disease vaccines", J Hyg (Camb) 1963b, 61: 337.

A widely used method for inactivating FMD virus by an aziridin is described by H. G. Bahnemann: "Inactivation of viral antigens for vaccine preparation with particular reference to the application of binary ethylenimine". Vaccine, 1999, 8, 299.

However, unlike FA, aziridins have no cross-linking reactivity and vaccines prepared from some unstable FMD (vaccine) strains showed short shelf lives. Therefore, some labile vaccine strains are first fixed with FA before inactivation is completed with an aziridin compound such as BEI. This method has been described in the following 3 publications:

Rowlands et al. (1972)—Stabilizing the immunizing antigen of foot-and-mouth disease virus by fixation with formaldehyde. Arch. Ges. Virusforsch. 39, 274–283;

Mowat et al. (1973)—Enhancement of immunizing potency of foot-and-mouth disease vaccine for cattle by treatment of the antigen with formaldehyde. Arch.ges.Virusforsch. 41, 365–370; and M M Rweyemamu et al. (1989)—Effect of formaldehyde (FA) and binary ethyleneimine (BEI) on the integrity of foot-and-mouth disease virus capsid. Rev. sci. tech. Off. Int. Epiz. 8, 747–767.

It is also known to inactivate the virus first with BEI and thereafter to cross-link or fix the inactivated virus particles or antigens with FA e.g. FMD virus antigen of the SAT2 Zim 7/83 strain.

A disadvantage of the known methods is that it takes relatively long (+/−2 days) to obtain satisfactory levels of inactivation, with the result that part of the virus antigen may degrade. Vaccines manufactured from such inactivated virus antigens are therefore relatively less effective, in use.

Furthermore, BEI does not always give satisfying inactivation. In practice, the extrapolated results sometimes indicate that there are still chances of the presence of surviving virus entities in a batch at the end of the inactivation (at 48 hours). This means that such a batch is not acceptable and must be destroyed.

OBJECTS OF THE INVENTION

Objects of the present invention are to provide methods of inactivating microorganisms and manufacturing vaccines, to provide vaccines manufactured by such methods and to provide kits incorporating such inactivated microorganisms, which are improvements of the known methods, vaccines and kits.

SUMMARY OF THE INVENTION

According to a first aspect of the invention there is provided a method of inactivating a microorganism including the step of applying to said microorganism a cross-linking agent simultaneously with a separate inactivant.

The applicants have surprisingly found that by using the cross-linking agent simultaneously with the inactivant, a synergistic or augmenting effect is achieved whereby the microorganisms are inactivated, not only more thoroughly but, also, in a relatively much shorter period in comparison with the prior art methods.

The Applicants have further found that vaccines manufactured according to the invention are effective in use, probably due to the fact that the inactivation period is relatively shorter and that the cross-linking agent fixes the antigens of the microorganism, as they become available. The Applicants believe that the antigens are thus preserved and not degraded and, therefore, vaccines manufactured according to the invention are expected to be more stable with longer shelf lives than the known vaccines. Also, the Applicants further believe that vaccines will become less dependent on strict cold-chain conditions during transport and use in the field.

The cross-linking agent may comprise an aldehyde.

The aldehyde may be a di-aldehyde.

Preferably the aldehyde is formaldehyde (FA).

The Applicants further believe that, at least in the case of FA, the cross-linking agent prepares the virus for inactivation by the inactivant.

The inactivant may be an aziridine compound. The aziridine compound may be an ethyleneimine.

Preferably the ethyleneimine is binary ethyleneimine (BEI).

The method may include the further step of stopping the inactivation process.

The inactivation process may be stopped by the addition of any one or more of sodium thiosulphate, sodium bisulfite, and trishydroxymethyl-aminomethane (Tris-buffer).

According to a second aspect of the invention there is provided a vaccine including a microorganism inactivated by the above method according to the first aspect of the invention.

According to a third aspect of the invention there is provided a method of manufacturing a vaccine including the steps of:

providing a pathogen;

inactivating the pathogen by applying to said pathogen a cross-linking agent simultaneously with a separate inactivant;

the cross-linking agent may also inactivate the pathogen (by its cross-linking activity).

The cross-linking agent may comprise an aldehyde.

The aldehyde may be a dialdehyde.

Preferably the aldehyde is formaldehyde (FA).

The inactivant may be an aziridine compound. The aziridine compound may be an ethyleneimine.

Preferably the ethyleneimine is binary ethyleneimine (BEI).

The method may include the further step of stopping the inactivation process.

The inactivation process may be stopped by the addition of any one or more of sodium thiosulphate, sodium bisulfite, and trishydroxymethyl-aminomethane (Tris-buffer).

The Applicants have further found that the above methods according to the invention are particularly effective in the inactivation of viruses and the preparation of vaccines for viral pathogens.

The virus may be of the family picoma viridae.

Preferably the virus is a foot-and-mouth disease virus, but it will be appreciated that the methods according to the invention will be effective in respect of most viruses and even other microorganisms.

According to another aspect of the invention there is provided a test kit including a microorganism inactivated by the above method of the invention. The inactivated microorganism may be in the form of an allergen or antigen for use in an ELISA.

BRIEF DESCRIPTION OF THE FIGURE

FIG. 1: Inactivation plots obtained with BEI alone (a) for one of the SAT vaccine strains and with BEI-FA (b–f) for 5 vaccine strains.

DETAILED DESCRIPTION OF THE INVENTION

A preferred embodiment of the invention will now be described by means of a non-limiting example.

In order to investigate the effect of BEI in combination with FA on FMD virus, two groups of viruses namely a test group and a control group were inactivated as set out below.

EXAMPLE

A method according to the invention for the inactivation of foot-and-mouth disease virus (FMDV) with a combination of formaldehyde (FA) and binary ethyleneimine (BEI) is set out below. A standard operating procedure (SOP) for the inactivation of FMDV for the purposes of FMD vaccine production is also explained in detail hereinafter. Reference is made only to the procedure followed in the test group. However, substantially the same procedures were followed in the case of the test and control groups, with the exception that in the test group, the BEI and FA was applied simultaneously, while in the control group, BEI was used on its own as the inactivating agent.

Definitions and Abbreviations Used Below

BEI: Binary ethyleneimine

BEA: 2-Bromoethylamine hydrobromide

NaOH: Sodium hydroxide

STS: Sodium thiosulphate

FA: Formaldehyde

ITT 1: First Inactivation Tank

IIT 2: Second Inactivation Tank

Chemicals:

Sodium hydroxide pellets (NaOH) p.a.—Merck

2-Bromoethylammonium bromide ($BrCH_2CH_2NH_3Br$)—Merck

β-Naphtol Violet solution formalin p.a. solution containing approximately 37% formaldehyde—Merck Materials and Equipment Measuring cylinder 1000 ml 5 liter sterile reagent bottle Sterile stirring magnet Sterile distilled water 10 ml sterile McCarthy bottles.

Fume hood pH meter (combined electrode) Orion

Weighing scale

Magnetic stirrer

Autoclave

Method

A filtered chloroform-treated SAT 2-Zim 7/83 virus culture is brought to a temperature of 30° C. and then inactivated with a combination of BEI and FA (BEI-FA). This combination inactivates FMD very rapidly (>2 log10 $ID_{50}$ per hour).

The culture was contained in a tank. Due to the fact that the BEI-FA may not enter some parts of the tank, such as dip-pipes, the virus might not be inactivated completely and might, at the end of the process, contaminate the inactivated virus antigen. Therefore, after approximately 4 hours the whole inactivation mixture is transferred into a second inactivation tank (with BEI only after 24 hours).

Samples are taken every 20 minutes to monitor the inactivation and verify the correct shape of the regression line. In the present method, in batches of 150 liter, the extrapolated inactivation plot must reach below -6.3 log10 $ID_{50}$ at the end of the inactivation (at 24 h). The inactivation is stopped by the addition of 2% STS, which neutralizes BEI.

Both, BEI and formaldehyde are toxic substances and should be handled with care. The BEI is prepared in a fume hood. After cyclisation (see below), the BEI solution should be handled with extreme care because it is highly toxic and probably carcinogenic. BEI remains must be neutralized with a 20% STS solution before it is discarded.

Note: The use of Tris or other quarternary ammonium salts e.g. for correction of the pH, should be omitted because they react with FA. Tris can also be used to stop further cross-linking/inactivation by FA.

Preparation of BEI and of BEI-FA (for 300 l Virus Harvest)

The preparation of BEI-FA solution must take place in a fume hood (at room temperature) as follows:

Dispose 2970 ml of sterile distilled water in a sterile 5-liter reagent bottle.

Add 21 g of NaOH to the 3 liter distilled water.

Add a sterile magnet and stir until all the NaOH has been dissolved. (To save time the NaOH can be prepared the day before the BEI is needed)

Take the pH of the NaOH solution and write the measured pH value on the bottle and on the record sheet.

Add 61.5 g BEI to the 3 liter of NaOH solution.

Add 1.5 ml of a 1% β-Naphtol violet solution to the BEI.

Allow cyclisation of BEI to take place for 1 hour at 37° C. on a magnetic stirrer.

Measure the pH after cyclisation. (pH range from 10 to 11)

Check the colour of the solution.

After cyclisation the color of the β-Naphtol violet has changed from purple into orange.

For inactivation with the BEI-FA combination, add 30 ml of formalin solution.

Inactivation Procedure With BEI Only

Add 10 ml of 0.1 M BEI per liter virus harvest to reach a final concentration of 1 mM.

Take during the first 6 hours of inactivation a sample (30 ml, see below) every hour.

After 24 hours of inactivation, when the virus titer is expected to be below zero (less than 1 virus particle per ml), add the same quantity of BEI and transfer the inactivation mixture to the second inactivation tank (ITT2).

Take a sample of 100 ml.

Check the pH of the sample.

At 48 hr add 10% of a 20% STS solution and stir (final STS concentration: 2%).

Take a sample of 600 ml for checking the pH and for the 'in vitro' safety, 146 S, and sterility tests (see respective SOPs).

Cool ITT 2 by flushing cold water through its jacket.

Now, the inactivated antigen can be transferred to the "Quarantine Zone" for further processing.

Inactivation Procedure With the BEI-FA Combination

Add 10 ml of 0.1M BEI-FA per liter virus harvest to reach a final concentration of 1 mM BEI and 0.04% of FA (approx. 1 mM).

Take during the first 3 hours a sample every 20 minutes.

After 4 hours of inactivation, when the virus titer is expected to be below zero (less than 1 virus particle per ml), transfer the inactivation mixture to the second inactivation tank (ITT2).

Take a sample of 100 ml.

After 20 hours of inactivation add 10% of a 20% STS solution and stir (final STS concentration: 2%).

Take a sample of 600 ml for checking the pH and for the 'in vitro' safety, 146S, and sterility tests (see respective SOPs).

Cool ITT 2 by flushing cold water through its jacket.

Now, the inactivated antigen can be transferred to the "Buffer Zone" for further processing.

Monitoring of the Inactivation Process

General

Both inactivation tanks are equipped with sampling devices that are steam-sterilized in between the sampling.

Sampling and Titration

Take samples of at least 30 ml (see below).

Split each sample immediately into 3 volumes of 8 ml and add them to sample bottles that contain 1 ml 20% STS and 1 ml fetal bovine serum (FBS) free of anti-FMD virus activity, giving final concentrations of 10% of FBS and 2% of STS. Store one sample at 4° C. and 2 samples, for backing up, at −70° C.

Take a sample of 100 ml at 4 hour, before the inactivation mixture is transferred to the second inactivation tank and measure the pH.

Take a final sample of 600 ml at the end of the inactivation.

The reduction in virus titre is monitored by titration in microtitre plates with IBRS cells. The titers are expressed as 10 log units per ml (e.g. 1 million infectious doses per ml makes a titer of 6) and are plotted graphically.

Down Stream Processing

Inactivated virus antigen was concentrated by routine ultra-filtration to approximately 2 liter. Samples of the concentrated antigen were taken and send for routine checks and controls (sterility, 146 S antigen yields, and ELISA), Other samples and the bulk of the concentrated antigen were stored at −70° C.

Experimental Vaccine

An experimental Al(OH)3-saponin vaccine was prepared from a mixture of all 5 FA-BEI-inactivated vaccine strains. The vaccines contained per 3 ml dose 0.8 μg 146 S antigen of each vaccine strain with the exception of SAT3 KNP90/3 of which 1.6 μg was added. 5 cattle were vaccinated with ¼ of a dose (0.75 ml). Blood-serum samples taken after the vaccination were tested in a virus-neutralisation assay.

Results Obtained With the Invention

A representative inactivation plot obtained with BEI alone is given in FIG. 1a. In our experience, with BEI alone, inactivation rates vary between 0.4 and 1.0 log per hour (see also Bahnemann, 1990) and sometimes, at low inactivation rates, the primary plots suggest some "tailing off".

Routinely, inactivation is carried out for 48 hours. At 24 hours a second portion of BEI is added. Thus, even at the lowest inactivation rates, sufficient safety can be expected, and final safety tests are passed.

In the enclosed FIGS. 1a to f, the inactivation plots obtained with BEI alone (a) for one of the SAT vaccine strains and with BEI-FA (b–f) for 5 vaccine strains, are shown.

The inactivation rates were varying from 2.0 (SAT1-SAR9/81, FIG. 1b) to more than 3 logs per hour (SAT2-ZIM 7/83 and SAT2 KNP-19/89/2, FIGS. 1d and 1e respectively, table 1) Thus, inactivation is from more than 20 to over a 100-fold faster if FA is added.

TABLE 1

Inactivation rates (with BEI-FA) of five SAT vaccine strains.

| Strain | Inactivation rate |
| --- | --- |
| SAT 1-SAR 9/81 | 2.0 log/hr |
| SAT 1-KNP 91/1 | 2.5 log/hr |
| SAT 2-ZIM 7/83 | 3.1 log/hr |
| SAT 2-KNP 89/2 | 3.3 log/hr |
| SAT 3-KNP 10/90-3 | 2.2 log/hr |

It is difficult to say what causes this synergistic effect. Under optimal conditions, FA alone inactivates at a rate of approx. 0.3 log/hr only (Barteling, 1984). Thus hardly any addition is to be expected to the much faster inactivation of BEI.

From these graphs it is clear that by the FA-BEI combination linear plots were obtained and virus titres were found to be reduced by more than 2 logs per hour. Thus already within 8 hours sufficient inactivation was reached for acceptable safety. In accordance, no surviving virus could be detected in a large (200-ml) sample taken after 6 hours, as was the case for the final samples (at 20 hr).

It should be noted that in the micro-titre system undiluted and 10-fold diluted samples were causing a cyto-pathogenic effect but this was due to the toxicity of the formaldehyde (or the FA-BEI combination) and no virus could be propagated from these cups.

Thus inactivation can be carried out within the time span of a working day or just overnight instead of the 48 hours required for the inactivation with BEI alone. This gives greater flexibility in weekly production schedules.

With BEI alone, antigen yields (of SAT-strains) were often reduced from 10 to 30 percent during the 48 hours of inactivation. No reduction in 146 S antigen concentration was observed after the 24 hr of inactivation with FA-BEI. Where conditions were otherwise identical, a reduction with approximately half that observed with BEI could be expected. The optimal yields are probably due to fixation of the antigen by the cross-linking action of FA (Barteling, 1984).

The results obtained after the vaccination of 5 cattle with the vaccine prepared from the 5 BEI-FA-inactivated antigens are presented in table 2.

TABLE 2

Mean virus neutralisation titres at 2 weeks post vaccination and challenge results. The animals were vaccinated with ¼ of a dose containing 0.2 µg of each of the SAT 1 and SAT 2 strains and 0.4 µg of SAT 3.

| Strain | Mean titer |
| --- | --- |
| SAT 1 KNP 196/91-1 | 1.8 |
| SAT 1 SAR 9/81-1 | 2.4 |
| SAT 2 KNP 19/8-/2 | 2.0 |
| Sat 2 Zim 7/83-2 | 2.3 |
| SAT 3 KNP 10/90-3 | 2.3 |

Challenge (at 3 weeks post vaccination) was carried out with SAT 1 KNP 196/91-1. Out of 5 animals 2 were protected and 1 was partly protected (1 lesion).

Considering the low quantities of antigen (and adjuvants) that were incorporated in the vaccines the vaccine performed quite well. The vaccines contained per 3 ml dose 0.8 µg per FMD vaccine strain and ¼ of a dose (0.75 ml) was injected.

At 2 weeks post vaccination, the lowest neutralising antibody response was against SAT 1 KNP 91/1(with a mean titre of 1.8 log) and, therefore, this strain was selected as challenge strain (table 2). Two animals were protected and one was partly protected, indicating a protection level of approximately 50% (1 PD 50). Because the injected vaccine dose contained approximately 0.4 µg per FMD virus type (e.g. of SAT1), these results indicate that (for the weakest antigen) per µg a protection level of approximately 2.5 PD 50 can be expected which is, in comparison with the industry standard, surprisingly good.

Stability of the 146 S antigen is an important parameter in the selection of new vaccine strain. By the cross-linking action of FA, which stabilises the 146 S antigen, this parameter becomes less critical and, therefore, the BEI-FA inactivation method will make the rapid introduction of new vaccine strains relatively easier.

Because of the fixation of the antigen by the cross-linking action of FA, the applicants expect the vaccines to be of superior stability. This is particularly important for developing countries (e.g. in Africa), where maintenance of cold chain conditions is not always possible.

It will be appreciated that the method of inactivation according to the present invention presents strongly augmented inactivation rates, where sufficient safety levels are reached within approximately 8 hours or less, in comparison with the +/−2 days with the known methods. Therefore, inactivation for 20 hours with the method of the invention does not leave any possibility for a dispute on the safety of a batch.

The new inactivation method according to the invention shortens the process of vaccine manufacture with at least one day. This makes a vaccine production system far more flexible and enables the process (including a chloroform treatment) to fit into a 4 days working week.

The Applicants further believe that during the method according to the invention, the FA fixes the virus antigens during the inactivation and, therefore, will result in relatively more effective vaccines with a relatively long shelf live.

Where the inactivation with BEI alone gives, under favorable conditions, inactivation rates of 0.5–1.0 logs per hour (Rweyemamu et al.), the 5 vaccine strains studied so far showed that method according to the invention presents inactivation rates from 2.0 to 3.3 logs (FIGS. 2b–2f, table 1). Therefore, the method of the invention can give a guarantee for sufficient inactivation within 8 hours. This also means that the inactivation can be carried out within the time frame of a working day. This is of great advantage in a vaccine production process (virus production, harvest, clarification, inactivation, and concentration of the antigen) which, according to the prior art until now only just fits into a full working week.

The applicants foresee that a test kit including a microorganism inactivated according to the above method of the invention can be prepared. In the test kit, the inactivated microorganism can be in the form of an allergen or antigen for use in an ELISA.

It will be appreciated that variations in detail are possible with methods, vaccines, and kits according to the invention without departing from the scope of the appended claims.

What is claimed is:

1. A method of inactivating a microorganism comprising applying to said microorganism a cross-linking agent simultaneously with an aziridine compound.

2. A method according to claim 1 wherein the cross-linking agent comprises an aldehyde.

3. A method according to claim 2 wherein the aldehyde is a di-aldehyde.

4. A method according to claim 2 wherein the aldehyde is formaldehyde (FA).

5. A method according to claim 1 wherein the aziridine compound is an ethyleneimine.

6. A method according to claim 5 wherein the ethyleneimine is binary ethyleneimine (BEI).

7. A method according to claim 1 further comprising stopping the inactivation process.

8. A method according to claim 7 wherein the inactivation process is stopped by the addition of any one or more of sodium thiosulphate, sodium bisulfite, and trishydroxymethyl-aminomethane (Tris-buffer).

9. A method of manufacturing a vaccine comprising providing a pathogen, inactivating the pathogen by applying to said pathogen a cross-linking agent simultaneously with an aziridine compound, and producing a vaccine from the inactivated pathogen.

10. A method according to claim 9 wherein the cross-linking agent comprises an aldehyde.

11. A method according to claim 10 wherein the aldehyde is a dialdehyde.

12. A method according to claim 10 wherein the aldehyde is formaldehyde (FA).

13. A method according to claim 9 wherein the aziridine compound is an ethyleneimine.

14. A method according to claim 13 wherein the ethyleneimine is binary ethyleneimine (BEI).

15. A method according to claim 9 further comprising the step of stopping the inactivation process.

16. A method according to claim 15 wherein the inactivation process is stopped by the addition of any one or more of sodium thiosulphate, sodium bisulfite, and trishydroxymethyl-aminomethane (Tris-buffer).

17. The method according to claim 9 wherein the pathogen is a viral pathogen.

18. The method according to claim 17 wherein the viral pathogen is of the family picorna viridae.

19. A method of manufacturing a vaccine comprising providing a viral pathogen, inactivating the pathogen by applying to said pathogen a cross-linking agent simultaneously with a separate inactivant, and producing a vaccine from the inactivated pathogen.

20. The method according to claim 19 wherein the viral pathogen is of the family picorna viridae.

21. A method according to claim 19 wherein the cross-linking agent comprises an aldehyde.

22. A method according to claim 21 wherein the aldehyde is a di-aldehyde.

23. A method according to claim 21 wherein the aldehyde is formaldehyde (FA).

24. A method according to claim 19 wherein the inactivant is an aziridine compound.

25. A method according to claim 24 wherein the aziridine compound is an ethyleneimine.

26. A method according to claim 25 wherein the ethyleneimine is binary ethyleneimine (BEI).

27. A method according to claim 19 further comprising stopping the inactivation process.

28. A method according to claim 27 wherein the inactivation process is stopped by the addition of any one or more of sodium thiosulphate, sodium bisulfite, and trishydroxymethyl-aminomethane (Tris-buffer).

* * * * *